United States Patent [19]
Thompson et al.

[11] Patent Number: 5,192,288
[45] Date of Patent: Mar. 9, 1993

[54] SURGICAL CLIP APPLIER

[75] Inventors: Todd Thompson, San Jose; Terrance Kloeckl, Palo Alto, both of Calif.; Peter F. Costa, Winthrop; William A. Holmes, Marblehead, both of Mass.; Jay Daulton, San Jose, Calif.

[73] Assignee: Origin Medsystems, Inc., San Carlos, Calif.

[21] Appl. No.: 888,723

[22] Filed: May 26, 1992

[51] Int. Cl.$^5$ ............................................. A61B 17/00
[52] U.S. Cl. ................................... 606/143; 606/142; 227/901
[58] Field of Search ...................... 606/139, 142, 143; 227/901

[56] References Cited

U.S. PATENT DOCUMENTS

| | | | |
|---|---|---|---|
| 3,086,208 | 4/1963 | Eby . | |
| 3,439,522 | 4/1969 | Wood . | |
| 3,665,924 | 5/1972 | Noiles et al. | 128/305 |
| 3,675,688 | 7/1972 | Bryan et al. | 140/93 |
| 3,683,927 | 8/1972 | Noiles | 128/334 |
| 3,777,538 | 12/1973 | Weatherly et al. | 606/142 |
| 3,819,100 | 6/1974 | Noiles et al. | 227/19 |
| 3,828,791 | 8/1974 | Santos | 128/321 |
| 4,086,926 | 5/1978 | Green et al. | 128/334 |
| 4,440,170 | 4/1984 | Golden et al. | 606/142 |
| 4,478,220 | 10/1984 | Di Giovanni et al. | 128/326 |
| 4,509,518 | 4/1985 | McGarry et al. | 128/325 |
| 4,527,725 | 7/1985 | Foslien | 606/143 |
| 4,616,650 | 10/1986 | Green et al. | 128/325 |
| 4,624,254 | 11/1986 | McGarry et al. | 128/325 |
| 4,674,504 | 6/1987 | Klieman et al. | 128/325 |
| 4,821,721 | 4/1989 | Chin et al. | 606/143 |
| 4,951,860 | 8/1990 | Peters et al. | 227/177 |
| 5,032,127 | 7/1991 | Frazee et al. | 606/143 |
| 5,035,692 | 7/1991 | Lydon et al. | 606/143 |
| 5,084,057 | 1/1992 | Green et al. | 606/142 |

Primary Examiner—Stephen C. Pellegrino
Assistant Examiner—Gary Jackson
Attorney, Agent, or Firm—Townsend and Townsend

[57] ABSTRACT

According to the present invention, improved apparatus and methods are provided for applying surgical clips to body tissue in inaccessible places and at various angles with particular usefulness in laparoscopic surgery. In one embodiment, the apparatus comprises a shaft having a distal end and a proximal end; means for advancing clips along the shaft toward the distal end with the legs of the clip oriented in a distal direction; means at the distal end of the shaft for rotating the clips relative to the shaft to orient the legs in a lateral direction and means for closing the legs of the clips after the rotation. The means for advancing usually comprises a movable belt disposed in the shaft having a plurality of retainers for holding clips; means for closing typically includes an anvil mounted at the distal end of the shaft and a hammer movable against the anvil. In another embodiment the apparatus further comprises means disposed at the proximal end of the shaft for actuating the hammer, which usually consists of a trigger pivotally mounted to a handle. In an exemplary embodiment, the trigger is ratcheted in stages, wherein one stage advances a clip, a second stage rotates a clip and a third stages closes a clip.

33 Claims, 11 Drawing Sheets

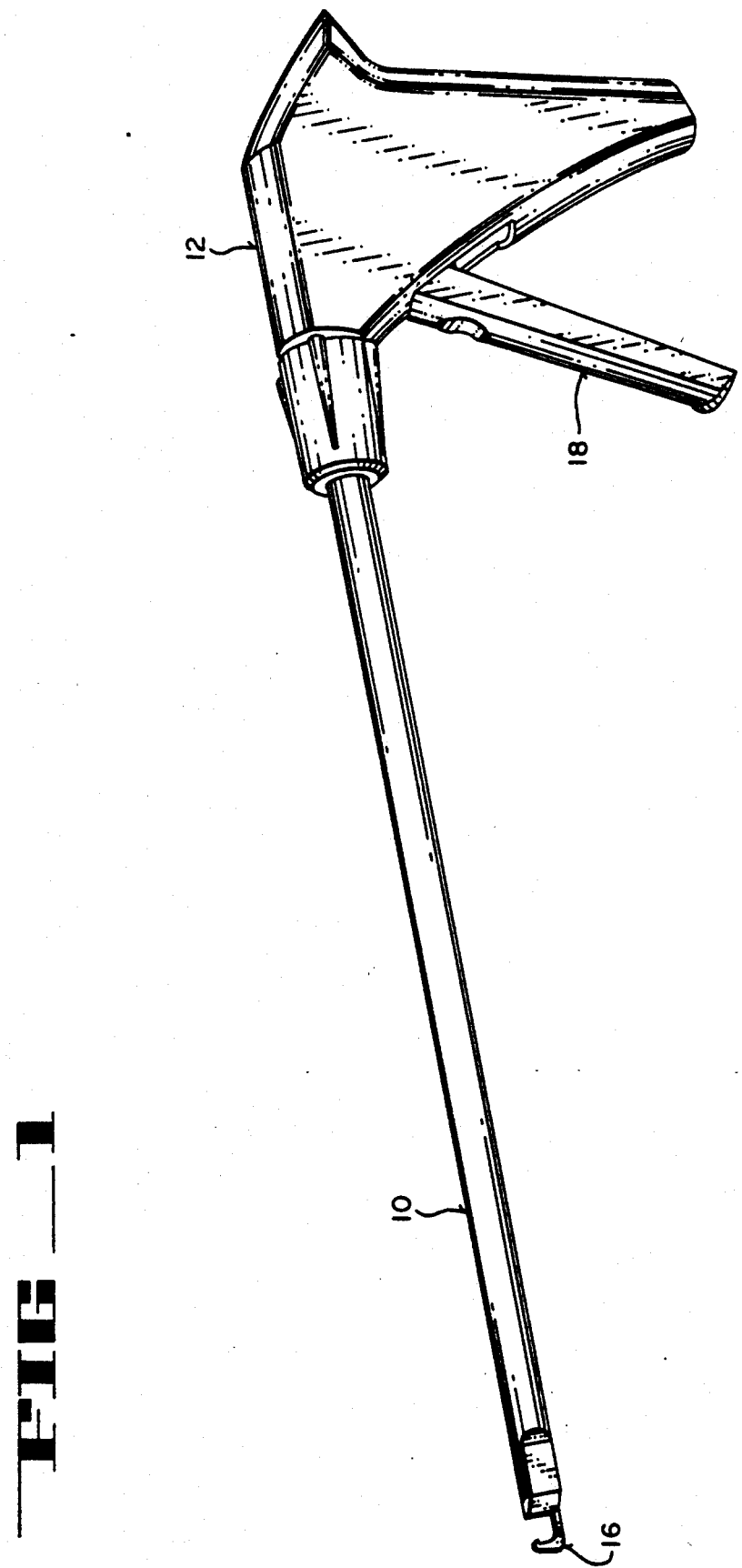

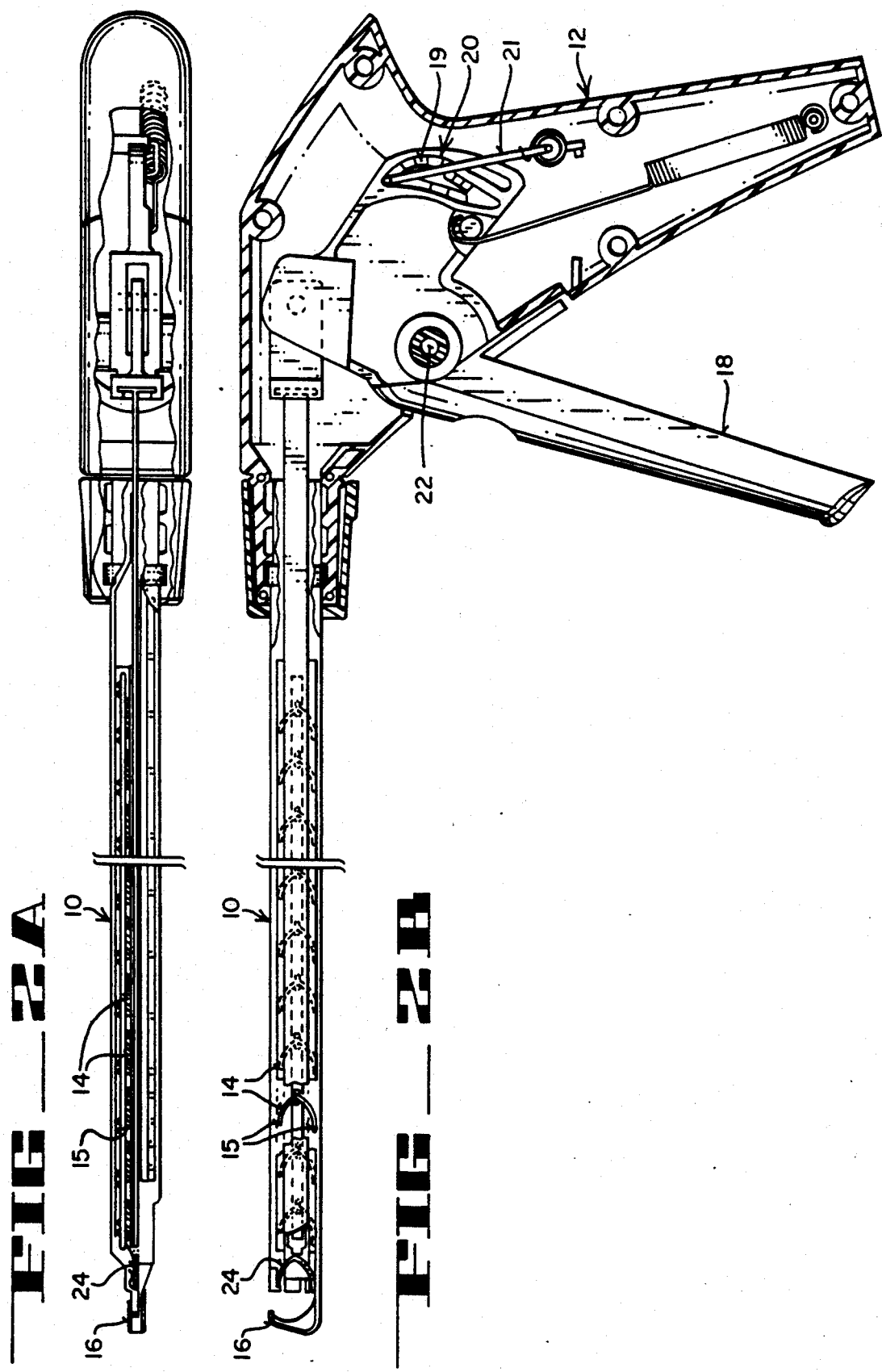

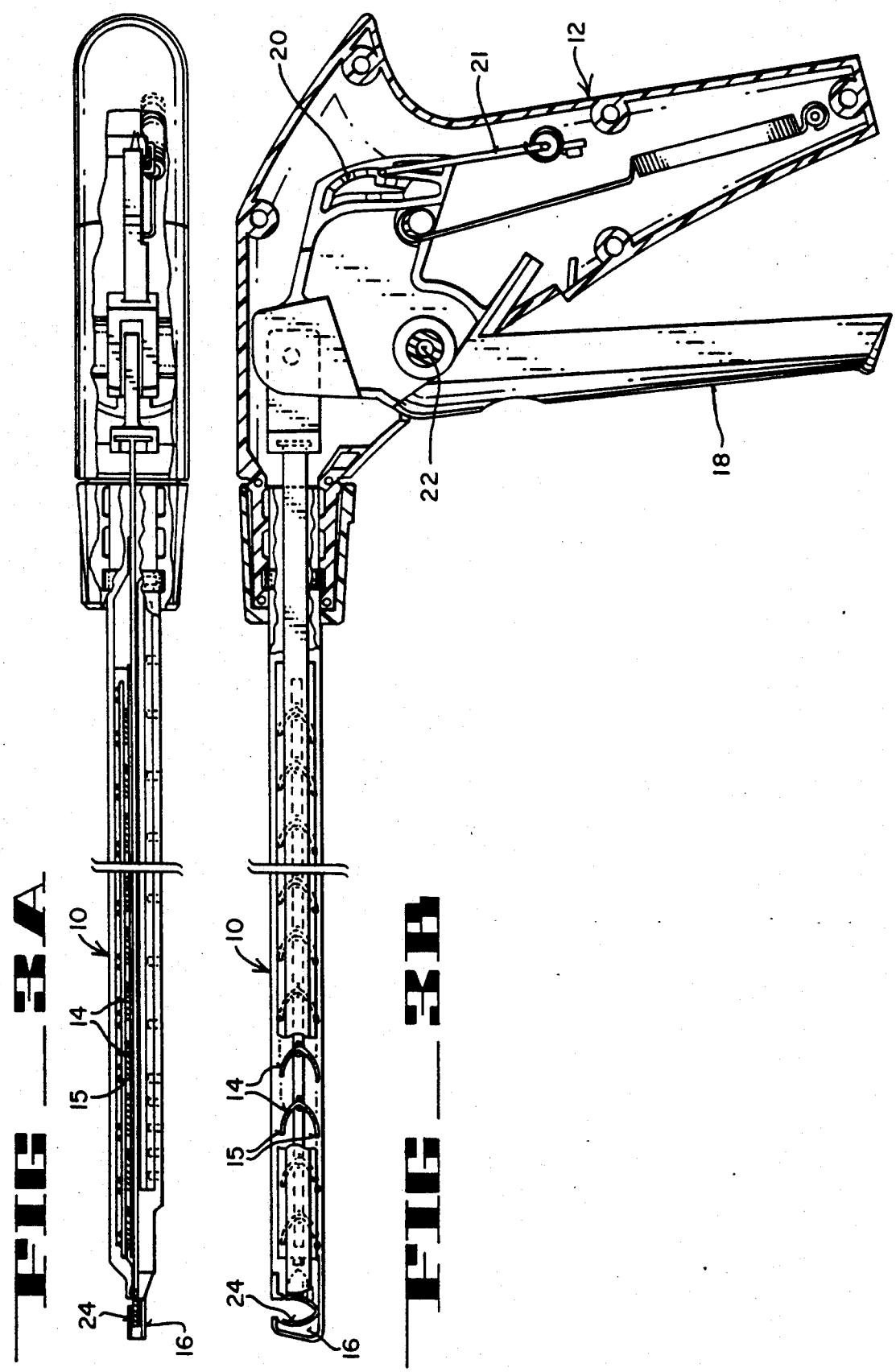

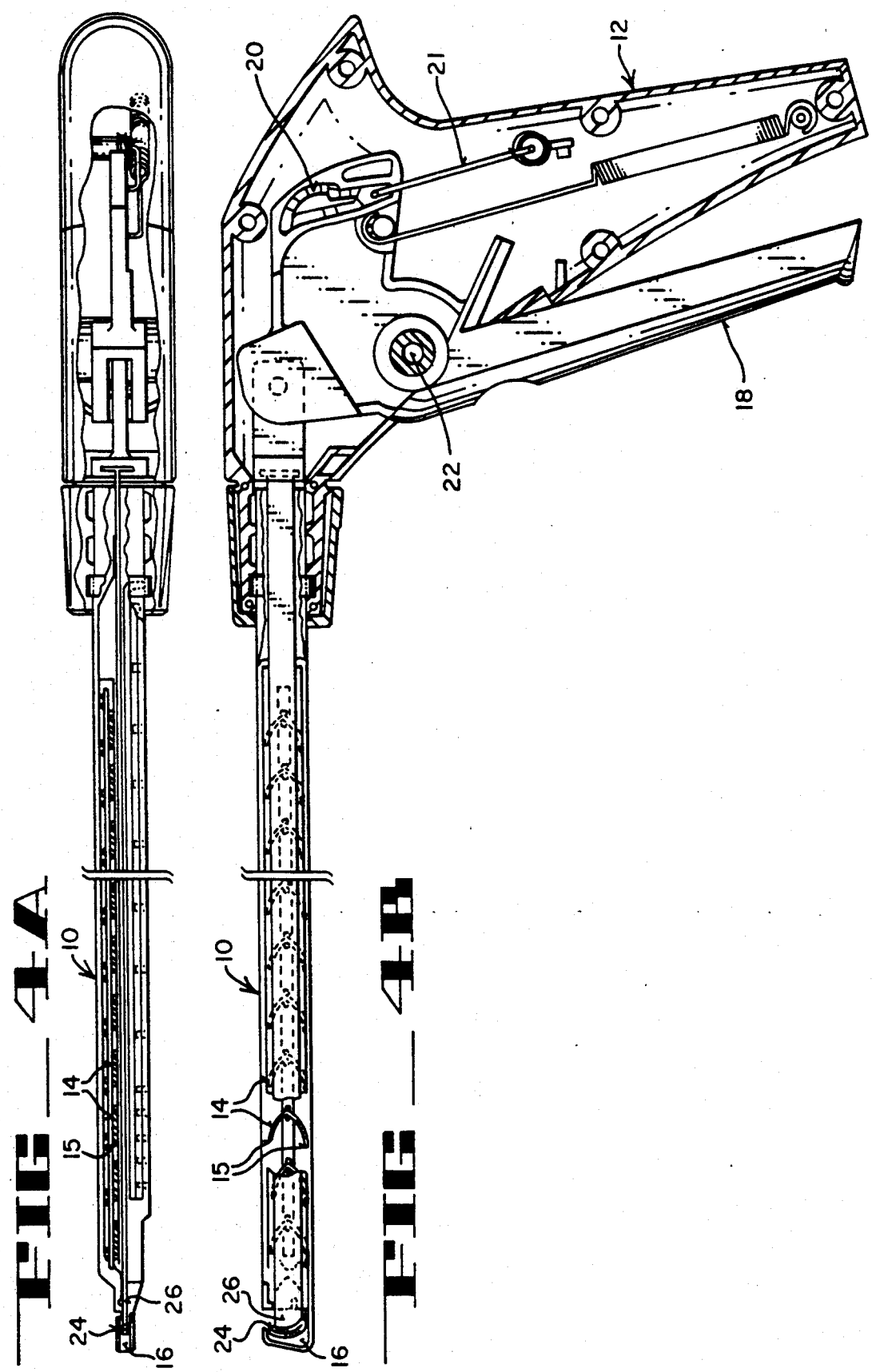

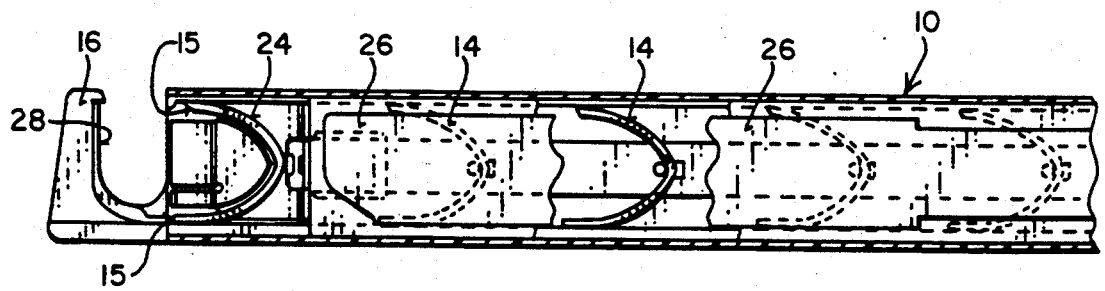
FIG_5A
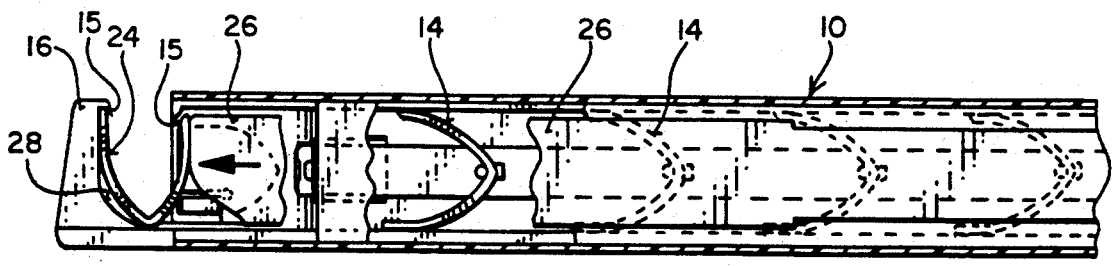
FIG_5B
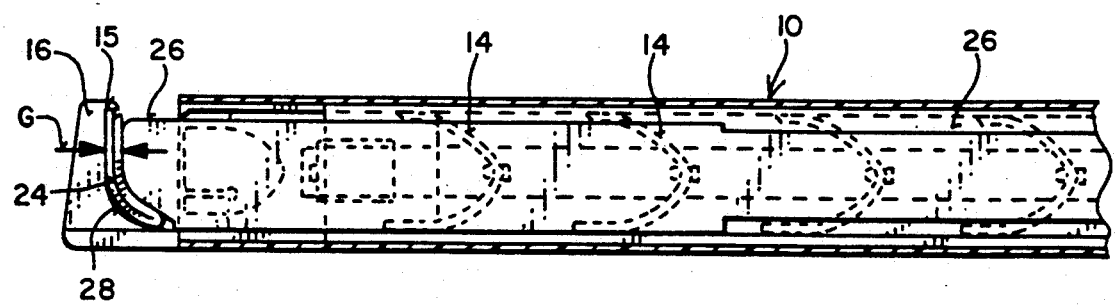
FIG_5C

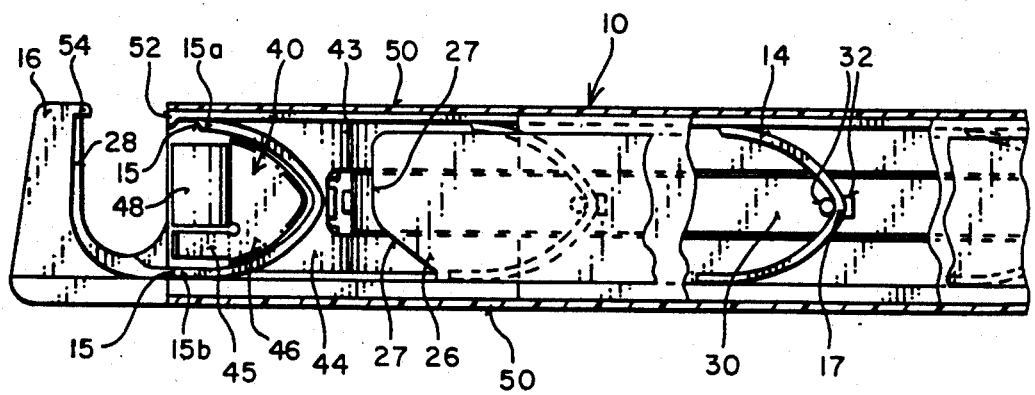
FIG_6A
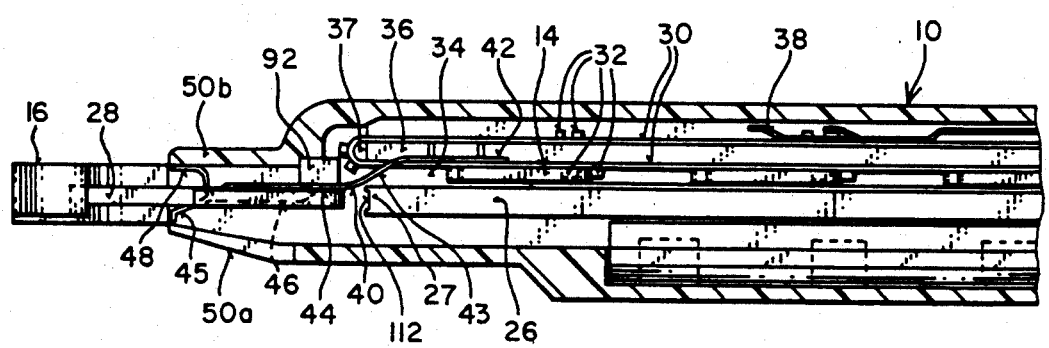
FIG_6B
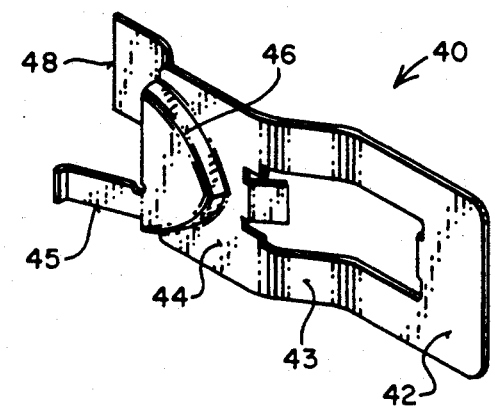
FIG_7

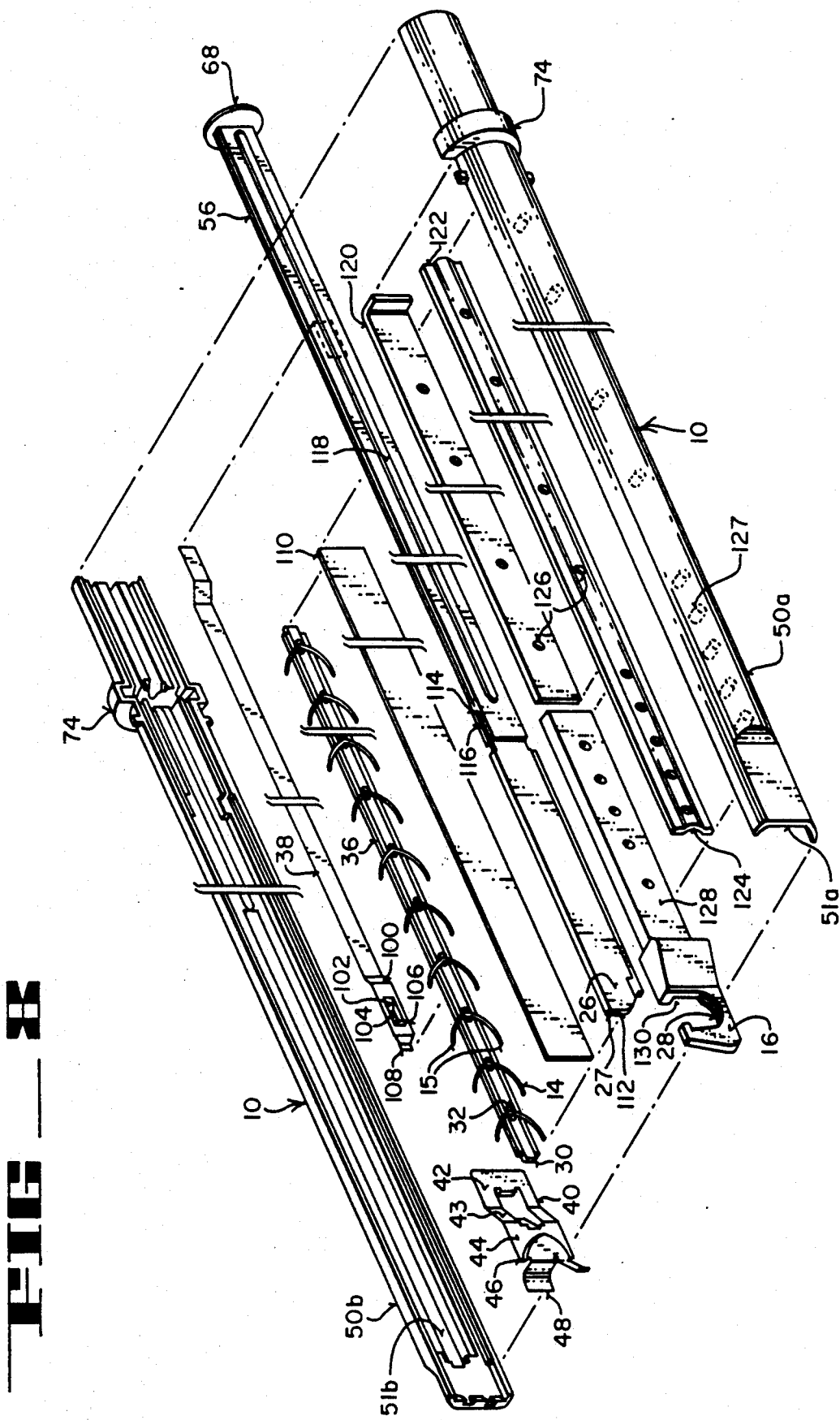

FIG_9A
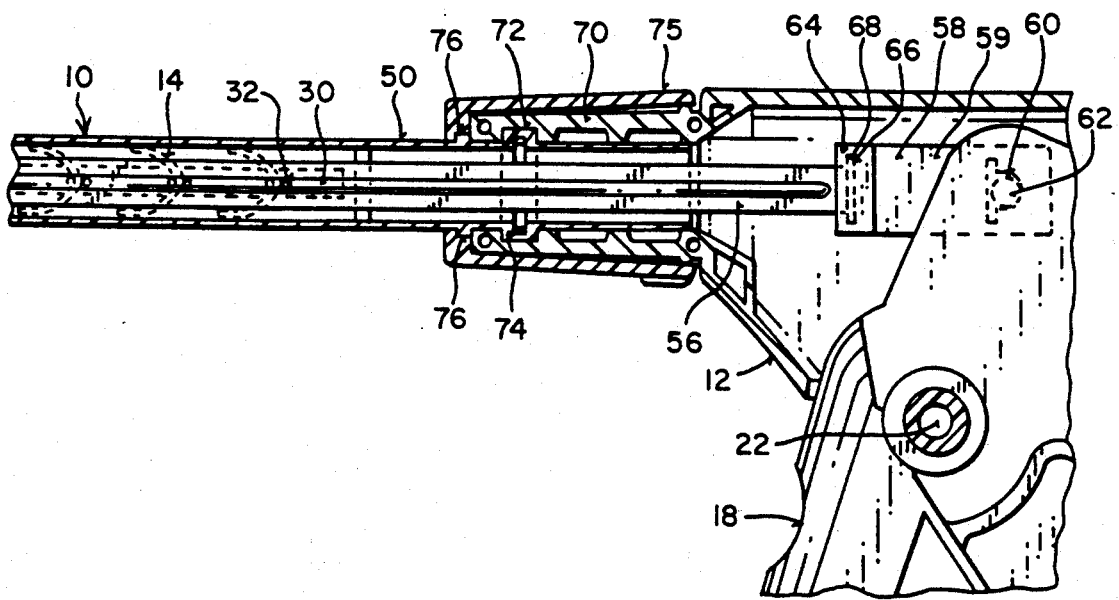
FIG_9B
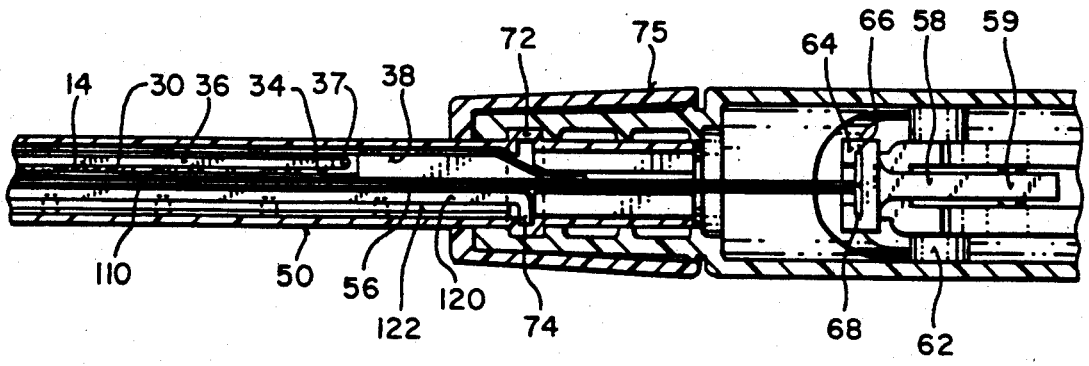

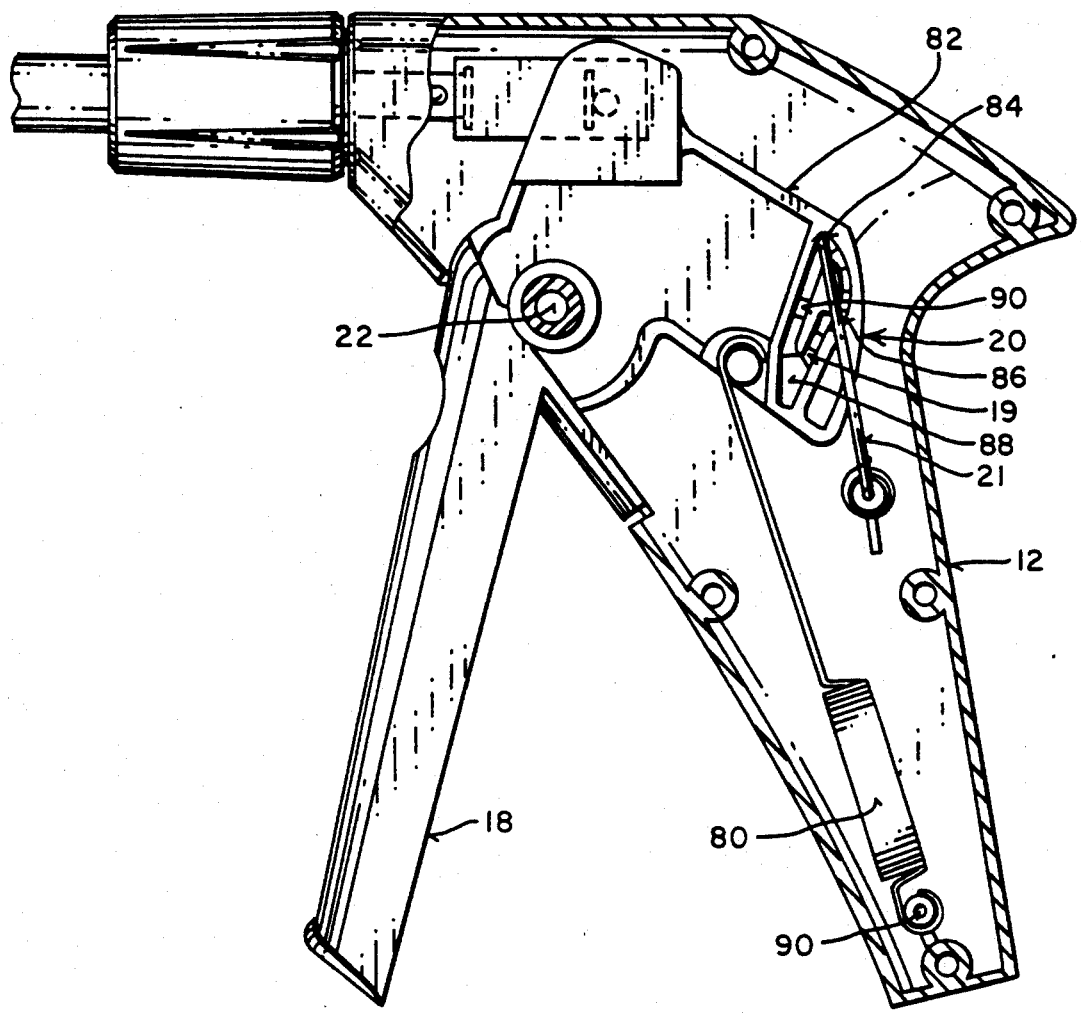
FIG_10A
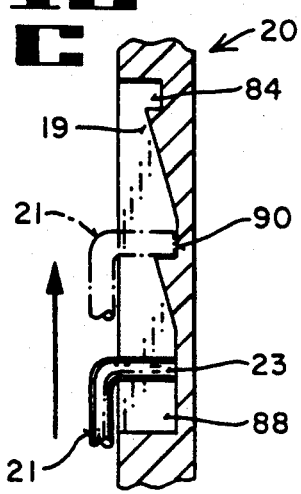
FIG 10C
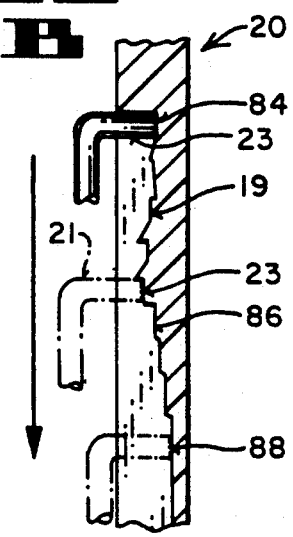
FIG 10B

FIG _ 11A
FIG _ 11B
FIG _ 11C    FIG 11D
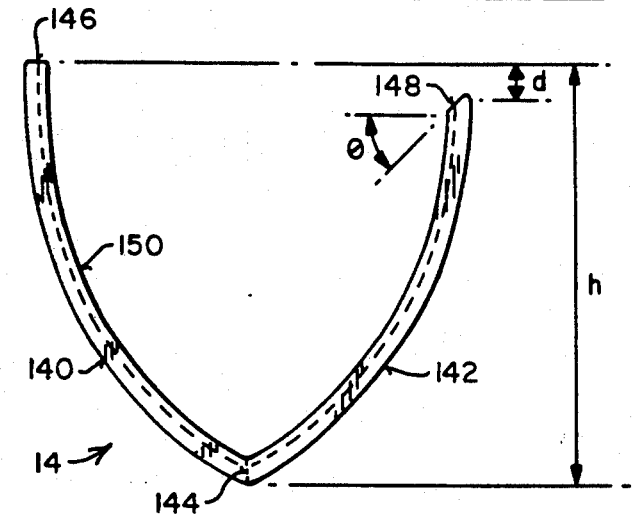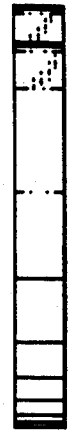
FIG 11E    FIG _ 11F
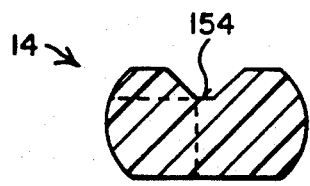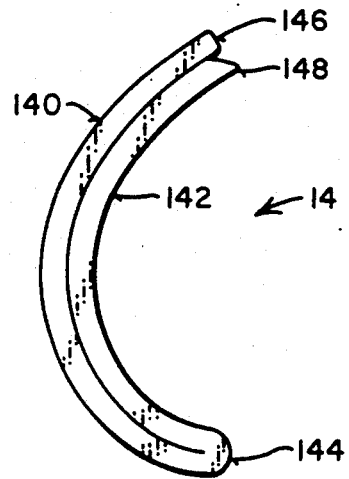

FIG _12A
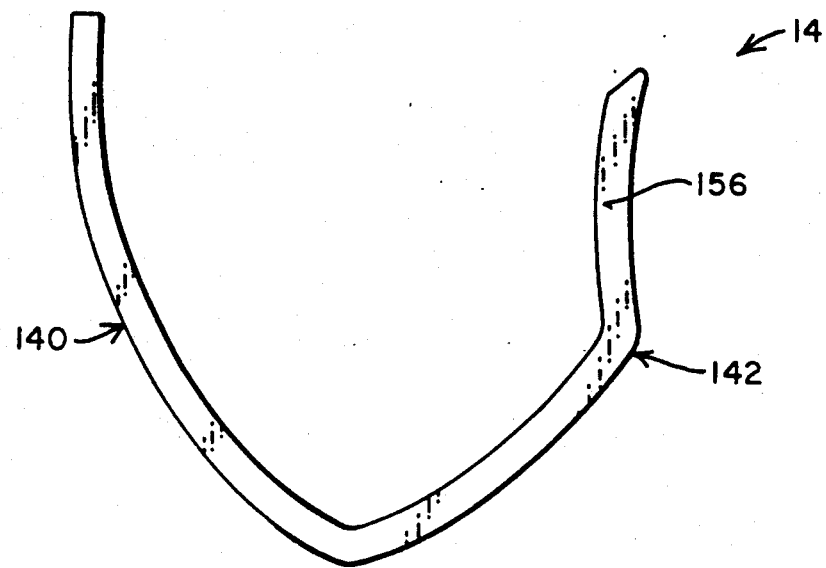
FIG _12B
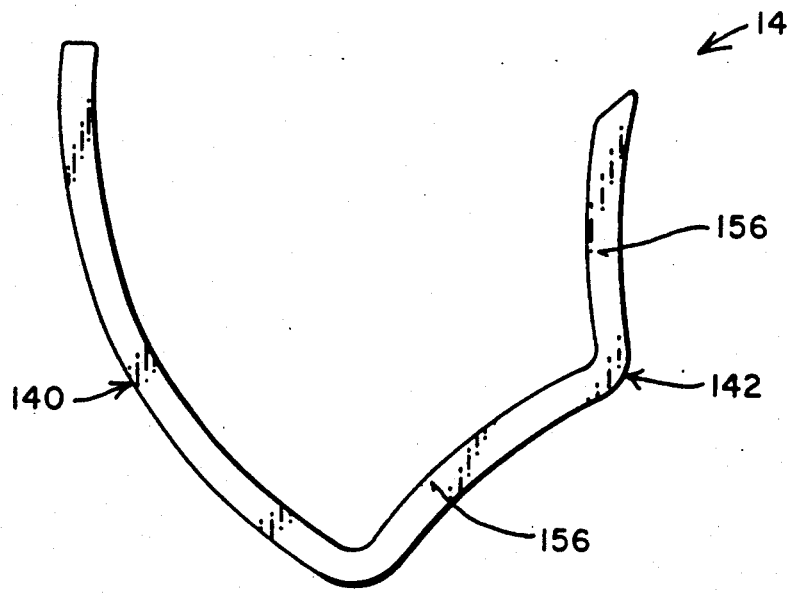

SURGICAL CLIP APPLIER

BACKGROUND OF THE INVENTION

The present invention relates generally to surgical instruments and more specifically to surgical clip appliers used for applying ligating clips to blood vessels and other tubular ducts or tissue.

In surgical procedures, it is frequently necessary to ligate ducts, such as blood vessels, or other severed tissue. For this purpose, it is well-known to use surgical clip appliers, such as that described in U.S. Pat. No. 3,439,522, to apply surgical clips to a duct or tissue to be ligated. Such clip appliers typically have a scissor-like construction, with a pair of movable handles which are grasped by the surgeon, and a pair of movable jaws opposite the handles into which a surgical clip is placed. Such clips usually have a pair of connected legs to form a U or V shape. When the handles are closed, the jaws close the legs of the clip together on the vessel or other tissue to be ligated.

In some surgical procedures, it is desirable to use a clip applier which is configured to allow tissue ligation in inaccessible areas of the surgical site. To address this need, a number of surgical clip appliers have been developed with the jaws extended from the handles at a distance, or with the jaws oriented at various angles. Examples are described in U.S. Pat. Nos. 3,777,538, and 4,440,170.

Other known clip appliers, such as that described in U.S. Pat. No. 4,616,650, provide for retaining multiple clips in the applier and feeding the clips toward the distal end of the applier, thereby permitting the surgeon to apply multiple clips at various places in the surgical site without removing the clip applier from the site to place another clip in the jaws. In some of these known devices, the clip applier is designed to accommodate an interchangeable cartridge containing multiple clips. An example is seen in U.S. Pat. No. 3,675,688.

In some surgical procedures, however, known clip appliers suffer certain drawbacks. In particular, known clip appliers have significant limitations when used in laparoscopic surgical procedures. Such procedures usually involve distending the abdominal cavity away from the underlying organs to improve access and visibility, using gas insufflation or a mechanical distension technique. Several small incisions are made in the abdomen through which are inserted trocar sleeves—plastic tubes designed to provide a sealed entryway into the abdominal cavity. Surgery is performed using long-handled instruments inserted through the trocar sleeves, with a lens connected to a video monitor providing visibility of the abdominal cavity.

Clip appliers used in laparoscopic surgery must be elongated so as to reach through the abdominal wall to the appropriate site, and preferably should not require removal from the abdominal cavity to reload clips after each clip is applied. The distal portion of such clip appliers must be of such dimension so as to pass through a trocar sleeve. Of particular importance is the orientation of the jaws at the distal end of the clip applier. During the course of surgery, ducts or tissue to be ligated will be oriented at various angles relative to the abdominal wall. Because of the limited range of motion afforded by the trocar sleeve, the surgeon depends on the orientation of the jaws to properly correspond with the angle of the duct or tissue to be ligated. In some cases, a surgeon may need to ligate a vessel or other tissue at an angle of up to 90° or more relative to the distal end of the clip applier. Further, because of the limited visibility of the surgical site and the limited maneuverability of instruments through the trocar sleeve, once a surgeon has positioned a clip applier at a desired site, s/he may want to apply two or more clips along a portion of duct or tissue without pulling the clip applier away from the site to position additional clips in the jaws.

In addition, the distally-oriented jaws of known clip appliers suffer from the inability to exert tension upon a duct or portion of tissue to which a clip is to be applied. Any repositioning of tissue must be achieved by pushing on the clip applier, exerting a compressive force on the tissue. This tends to push the tissue against underlying tissue, which may obstruct visibility, and can interfere with the application of the clip. Moreover, the unintentional application of a clip to underlying tissue, e.g. an organ or blood vessel, can pose a serious risk to the patient.

For these reasons, it would be desirable to provide improved methods and apparatus for applying surgical clips which permit application of multiple clips without removing the apparatus from the surgical site, and at the same time orient the clips at various angles relative to the distal end of the clip applier, including perpendicular thereto. The methods and apparatus should be usable in laparoscopic surgery and other such procedures wherein a very small incision is made. In particular, the apparatus should be capable of passing through a trocar sleeve having a diameter of 10 mm. It would be particularly desirable if the clip applier jaws could be rotated about 360° from a point outside of the surgical area and proximate to the point where the clip applier is held by the user. The apparatus and method should further allow the surgeon to apply clips in a controllable manner, permitting the clip to be closed as slowly or quickly as the surgeon desires. In addition, the apparatus and method should allow the user to exert tension on a portion of tissue for more effective positioning, so as to improve visibility of the tissue to be ligated, as well as to avoid interference with nearby tissue.

SUMMARY OF THE INVENTION

According to the present invention, improved apparatus and methods are provided for applying surgical clips to body tissue in inaccessible places and at various angles with particular usefulness in laparoscopic surgery. In one embodiment, the apparatus comprises a shaft having a distal end and a proximal end; means for advancing clips along the shaft toward the distal end with the legs of the clip oriented in a distal direction; means at the distal end of the shaft for rotating the clips relative to the shaft to orient the legs in a lateral direction and means for closing the legs of the clips after the rotation.

The means for advancing usually comprises a movable belt disposed in the shaft having a plurality of retainers for holding clips. The means for closing typically includes an anvil mounted at the distal end of the shaft and a hammer movable against the anvil. In another embodiment, the apparatus further comprises means disposed at the proximal end of the shaft for actuating the hammer, which usually consists of a trigger pivotally mounted to a handle. In an exemplary embodiment, the trigger is ratcheted in stages, wherein one stage advances a clip, a second stage rotates a clip and a third stages closes a clip.

The present invention further provides a surgical clip for use in a clip applier. The improved surgical clip has a pair of legs, one leg being longer than a second leg, the legs connected by a bridge portion to form a modified V shape. The longer leg configuration permits the clip to be closed in a curve with the tips of the legs substantially even in the closed configuration. The clip is further provided with surface features, such as slots drilled through the legs, to improve the grip of the clip on tissue.

The method of the present invention comprises, in one embodiment, the steps of providing a clip applier having means for closing a clip and means for advancing a clip to the closing means, the means for closing defining a slot open in a lateral direction; positioning the clip applier such that the slot surrounds the tissue to which a clip will be applied; advancing a clip with legs oriented in a distal direction; rotating the clip into the slot such that the tissue lies between the legs of the clip; and closing the clip on the tissue. In a further embodiment, the method provides for rotating, closing and advancing clips using a trigger having three stages corresponding to each of the forementioned steps.

The methods and apparatus of the present invention have several important advantages over known clip appliers. Clips may be applied in inaccessible areas at various angles. Multiple clips may be applied without removing the clip applier from the surgical site. The direction of the surgical clip may be adjusted about 360° by the surgeon at a point near the handle of the apparatus. Importantly, a first clip can be applied to a tissue site, and a second clip may be advanced and applied to an adjacent site without removing the clip applier from the tissue. Further, the clip applier is configured to pass through a 10 mm trocar sleeve, permitting its use in laparoscopic surgery and other surgical procedures where a very small incision is made. Also significant is the capability for applying a tensile force on tissue positioned in the anvil of the clip applier, so as to provide improved visibility in laparoscopic procedures, as well as to reposition the tissue away from nearby tissue to avoid interference therewith.

A further understanding of the nature and advantages of the invention may be realized by reference to the remaining portions of the specification and the drawings.

DESCRIPTION OF THE DRAWINGS

FIG. 1 is a perspective view of a clip applier constructed in accordance with the principles of the present invention.

FIGS. 2A and 2B are front and top cross-sectional views of the clip applier of FIG. 1 before a clip has been advanced into the anvil.

FIGS. 3A and 3B are front and top cross-sectional views of the clip applier of FIG. 1A with a clip in position in the anvil before closing.

FIGS. 4A and 4B are front and top cross-sectional views of the clip applier of FIG. 1A wherein a clip has been closed in the anvil.

FIGS. 5A-5C are close-up front cross-sectional views of the distal end of the clip applier of FIG. 1A showing a clip prior to being advanced into the anvil, in position in the anvil before closing, and in a closed position in the anvil, respectively.

FIGS. 6A and 6B are front and top cross-sectional views of the distal end of the clip applier of FIG. 1A.

FIG. 7 is a perspective view of the whip of the clip applier of FIG. 1A.

FIG. 8 is a perspective assembly view of the distal end of the clip applier of FIG. 1A.

FIG. 9A and 9B are front and top cross-sectional views of the proximal end of the barrel of the clip applier of FIG. 1.

FIG. 10A is a front and side cross-sectional views of the handle of the clip applier.

FIGS. 10B and 10C are side cut-away views of the ratchet mechanism in the handle of FIG. 10A.

FIGS. 11A and 1B are front and top elevational views of a surgical clip constructed in accordance with the principles of the present invention with legs straightened to illustrate surface features.

FIGS. 11C-11E are front and side elevational and side cross-sectional views of the surgical clip of FIGS. 11A and 11B in an unclosed configuration.

FIG. 11F is a front elevational view of the surgical clip of FIGS. 11A and 11B in a closed configuration.

FIGS. 12A and 12B are front elevational views of alternate embodiments of a surgical clip constructed in accordance with the principles of the present invention.

DESCRIPTION OF SPECIFIC EMBODIMENTS

Referring to FIG. 1, the surgical clip applier of the present invention includes, in a preferred embodiment, a tubular shaft or barrel 10 rotatably coupled to a handle 12, the barrel 10 holding a number of surgical clips (not shown) oriented in the barrel such that clip legs point toward the distal end of the barrel, as will be described in detail below. An anvil 16 is disposed at the distal end of the barrel and forms a slot having an open side facing laterally from the barrel. In a preferred embodiment, the slot in anvil 16 is oriented at 90° relative to the barrel 10. However, it should be understood that the slot may be configured at any of various angles from 5° up to approximately 170° relative to barrel 10.

Referring now to FIG. 2A, a lever 18 is pivotally mounted to handle 12 at pivot point 22 and includes a ratcheting mechanism 20 including a grooved track 19 and a pawl 21 following track 20. As shown in FIGS. 3A and 3B, when lever 18 is pulled toward handle 12, the distal-most clip 24 is positioned in the anvil 16 with legs 15 pointing laterally. At the same time, pawl 21 has advanced in track 20 reaching an intermediate rest position as will be described more fully below.

As shown in FIGS. 4A and 4B, when the lever 18 is pulled to a position nearest handle 12, distal-most clip 24 is closed against anvil 16 by hammer 26 which extends from the interior of barrel 10.

The three major stages of closing distal-most clip 24 are shown in detail in FIGS. 5A through 5C. In FIG. 5A, distal-most clip 24 is in a position at the distal end of the barrel 10 with legs 15 pointing distally. The distal end of hammer 26 is in a position toward the proximal end of the barrel relative to clip 24. In the position of FIG. 5B, lever 18 has been pulled toward handle 12 and hammer 26 has been translated distally, pushing on clip 24 to rotate the clip along the curved track 28 of anvil 16, so that legs 15 of the clip 24 are oriented in a lateral direction. In FIG. 5C, lever 18 has been pulled to the fullest proximal position, translating hammer 26 further distally, closing the clip 24 against track 28 of anvil 16.

The construction of the distal portion of the barrel of the clip applier is illustrated in FIGS. 6A and 6B. Clips 14 are retained in retainers 32 on belt 30. The belt 30 is composed of a flexible material, for example, molded plastic, or a metal such as nickel, and is sufficiently rigid to carry clips 14 without deforming away from the surface of belt track 36. In an exemplary embodiment, belt 30 is electroformed nickel with a thickness of 0.001"-0.002". Retainers 32 have a short distal portion separable from a longer proximal portion by a distance equal to or slightly less than the thickness of clips 14 at bridge 17. Bridge 17 fits snugly between the distal and proximal portions of retainer 32. Belt 30 is disposed on belt track 36 having rounded ends 37 about which belt 30 is rotatable. Clips 14 are guided in clip space 34 adjacent belt 30, shown in FIG. 6B. Clips 14 are advanced in a distal direction along barrel 10 by movement of belt 30 around belt track 36. The belt is advanced by belt puller 38, which engages and pulls empty retainers 32 in a proximal direction on the non-clip-carrying side of the belt 30.

Clips advanced by belt 30 along clip space 34 encounter whip 40 at the distal end of clip space 34. Typically, whip 40 is made of sheet metal or other smooth, hard and resilient material. Whip 40, as illustrated in FIG. 7, has a first surface 42 parallel to the belt and situated so as to lie between the belt and the distal-most clip retained thereon. As the clip advances further distally, the legs of the clip encounter ramp 43 which guides the legs 15 of the clip out of the plane in which the clips are carried on belt 30. At this point, the bridge 17 of clip 24 is still retained in retainer 32. As the belt continues to advance, legs 15 move up ramp 43 and bridge 15 is forced out of retainer 32, the clip being left in a position with legs 15 against ridge 46 of whip 40.

It can be seen that, in a preferred embodiment, clips are fed on belt 30 in clip space 34, which is disposed laterally of the central axis of barrel 10. On the other hand, in order to optimize loading when the clip is closed, hammer 26 is disposed in the center of barrel 10 and is translated along the central axis. Whip 40 transfers clips from the offset path of feeding to a central position for engagement by hammer 26 and closing against anvil 16. This configuration maximizes the use of space within barrel 10, which is designed to be insertable through a 10 mm trocar sleeve, while optimizing loading through the clip applier when the clips are closed.

Support 48 of whip 40 rests against the inner surface of tube half 50b of barrel 10, and provides resilient support for the distal end of whip 40. A guide arm 45 extends from the distal end of the whip for engaging a lower leg 15b of a clip (FIG. 6A) as it is advanced into the anvil, thereby ensuring leg 15b is guided into track 28.

Once distal-most clip 24 is on surface 49 of whip 40, it is in a position for engagement by hammer 26. The distal end 27 of hammer 26 pushes on bridge 17 of clip 24, forcing clip 24 over ridge 46 of whip 40. Support 48 of whip 40 allows whip 40 to resiliently give way as the clip 24 is pushed over ridge 46 by hammer 26. Ridge 46 is configured in a shape complementary to that of clips 14 so as to align clip 24 with legs 15 pointing symmetrically in the distal direction as the clip is advanced distally.

As clip 24 is pushed distally, outer leg 15a, shown in FIG. 6A, engages stop 52 at the distal end of barrel 10. Stop 52 obstructs movement of leg 15a, while leg 15b continues to move distally under the force of hammer 26. Leg 15b rotates about stop 52 and is guided by portions of guide arm 45 of the whip and track 28 in anvil 16 until the clip is in the position shown in FIG. 3A or 5B. Further distal movement of hammer 26 pushes leg 15a over stop 52 and toward leg 15b.

Track 28 in anvil 16 is usually curved from the bottom of the slot to the end point 54 of the track. Track 28 is further recessed in anvil 16 to allow clips to be rotated into the anvil without interfering with tissue positioned therein. The distal end 27 of hammer 26 is of a shape conforming to the shape of track 28 in anvil 16. As the hammer closes the clip, legs 15a and 15b are formed into the shape of track 28 and distal end 27, leaving legs 15a and 15b in a curved configuration when the clip is closed, as shown in FIG. 5C.

By closing the clip in such a curve, several benefits are obtained. First, clips closed on tissue in such a curved shape have been found to have improved grip over clips closed with the legs straight. Second, by using a curved hammer and anvil, the size of the clip applier relative to size of clips it can apply is minimized. Thus, the clip applier can be designed to be insertable through a 10 mm trocar sleeve while accommodating clips with longer legs than those which clip appliers with straight-leg closure can accommodate if designed for a trocar of similar size. The clip applier of the present invention, designed for a 10 mm trocar sleeve, is preferably capable of applying clips with legs at least 0.290 inches in length, from the apex of the clip to the tip of the shortest leg along the gripping surface.

The manner of rotating clips in the clip applier of the present invention is of particular importance. As seen in FIGS. 6A–6B, clip 24 rotates about stop 52 with leg 15b in track 28. The axis of clip rotation can lie anywhere in the area between and including the legs of the clip, the axis being perpendicular to the plane in which the clip lies. This allows a clip to be rotated from a distal orientation in the barrel 10 to a lateral orientation in anvil 16 without substantially entering the space in the slot of anvil 16. Thus, if the slot is positioned about a piece of tissue or duct, it need not be removed in order to rotate a clip into position in the anvil for closing. The clip can rotate into position without interference with tissue in the slot.

The assembly of the various components of barrel 10 is illustrated in FIG. 8. A pair of opposing tube halves 50a, 50b extend from the handle 12 to the anvil 16. Flange 74 at the proximal end of the tube halves is rotatably coupled to the handle as described below. Preferably tube halves 50a, 50b are a translucent plastic which provides rigidity to the barrel and permits the interior components of the barrel to be visible. The interior surfaces 51a, 51b of tube halves 50a, 50b are configured to form several channels in which the components of the barrel are nested. Tube halves 50a, 50b are preferably fastened to each other via tabs (not shown) along their longitudinal adjoining edges. Alternatively, adhesive or ultrasonic welding may be used to bond the halves 50a, 50b together.

Belt puller 38 is disposed between right tube half 50a and belt 30, belt 30 being disposed about belt track 36. Belt puller 38 has a proximal portion parallel to and separated from belt 30 by a gap so as not to interfere with belt movement. Near the distal end of belt puller 38 a raised portion 100 extends into a plane immediately adjacent belt 30. Raised portion 100 has a cutout section 102 from which a leg 104 is bent away from the surface of raised portion 100 and toward right tube half 50b. Tooth 106 at the distal end of cutout 102 is angled toward the surface of belt 30, preferably at about 20°, so as to engage retainers 32 when the belt puller moves in a proximal direction, but to ride over retainers 32 when the belt puller moves in a distal direction. Distal end 108 of belt puller 38 extends from the raised portion 100 back toward tube half 50b, distal end 108 and leg 104 providing resilient supports to maintain the position of raised portion 100 and tooth 106 immediately adjacent belt 30.

Clips 14 are carried by belt 30 in retainers 32 on the side of belt track 36 opposite that engaged by belt puller 38. The tips of clip legs 15 are guided by the interior surface 51b of tube half 50b forming clip space 34. Whip 40 is disposed in a position such that planar portion 42 lies between clips 14 and belt 30 at the distal end of belt track 36.

Clip wall 110 is disposed adjacent belt 30 and parallel thereto to provide a surface to retain clips 14 in position and guide them to the distal end of the barrel without interference from the other components in barrel 10. Hammer 26 coupled to a hammer extension 56 is disposed adjacent clip wall 110. Distal end 27 of hammer 26 has a groove 112 slightly wider than the width of clips 14 for greater precision and reliability in engaging the clips. The proximal end 114 of hammer 26 is of a reduced thickness to fit within slot 116 at the distal end of hammer extension 56 to which it is fixed by welding or other known means. Hammer extension 56 has a longitudinal rib 118 providing increased rigidity. A flange 68 at the proximal end is coupled to the handle as described below. Hammer 26 is disposed in a position such that groove 112 in distal end 27 engages clips residing on surface 44 of whip 40 when hammer extension 56 and hammer 26 are extended distally.

Structural members 120, 122 are disposed adjacent hammer 26 and hammer extension 56. Left structural member 122 has a longitudinal rib 124 providing rigidity thereto, and is welded to structural member 120. Structural members 120, 122 are fastened to left tube half 50a via pins 127 extending from left tube half 50a and inserted through holes 126, the pins being secured by heating and flattening the ends or by other known means.

Anvil 16 has an extension 128 which fits between tube halves 50a, 50b and is usually welded to one of structural member 120, 122. Extension 128 has a channel 130 into which belt track 36, belt 30 and whip 40 extend. Thus, when a clip 24 is disengaged from belt 30 by ramp 43 of whip 40, the clip resides on surface 44 with legs 15 within channel 130 of anvil 16. As hammer 26 pushes a clip 24 from whip 40 toward the anvil, the lower clip leg 15b engages track 28 in anvil 16 which guides the clip through its rotational motion.

Referring now to FIGS. 9A and 9B, the proximal end of the barrel 10 will be more fully described. Barrel 10 is rotatably fixed to handle 12 by collar 70 having an internal cylindrical aperture 72 for trapping flange 74 at the proximal end of barrel 10. A rotation knob 75 is disposed around collar 70 and engages features 76 on the exterior of tube halves 50a, 50b, permitting the barrel 10 to be rotated by the user from a point near the handle and outside the surgical site.

Tube halves 50a, 50b extend into collar 70 of handle 12, with flange 74 being engaged in aperture 72, as shown in FIG. 9A. Belt track 36, belt 30, clip wall 110 and left tube structure 122 terminate at a point distally of aperture 72 in collar 70. Right structural member 120, fastened to left structural member 122 and left tube halve 50a, extends into collar 70 and is formed at a right angle into flange 74 of tube half 50a so as to rotate therewith.

Actuation of the hammer 26 at the distal end of the barrel 10 is accomplished by hammer extension 56 coupled to hammer 26 and extending from the hammer's proximal end to link 58 in handle 12. Link 58 has a proximal portion 59 pivotally coupled to handle 18 by pin 62 disposed in slot 60 of link 58. The distal portion 64 of link 58 has a cylindrical aperture 66 in which flange 68 of hammer extension 56 is trapped. This configuration permits hammer extension 56 to be rotated with barrel 10.

Belt puller 38, as shown in FIG. 9B, extends from the distal portion of the barrel 10 parallel to the surface of the belt 30 and, at a point proximally of the proximal end of clip wall 110, fastens to hammer extension 56 by welding or other known means. Thus, belt puller 38 acts in unison with hammer extension 56 according to the position of lever 18.

In an exemplary embodiment, collar 70, aperture 66 in link 58 and the body of handle 12 are configured with an openable exterior structure so as to permit barrel 10 to be removed from handle 12, allowing barrels to be interchanged with a single handle.

In operation, when lever 18 is in the position shown in FIG. 2A, link 58 is in its most proximal position, as are hammer extension 56, hammer 26, and belt puller 38. As lever 18 is pulled toward handle 12, link 58 is moved in a distal direction thereby pushing hammer extension 56 distally, pushing hammer 26 against clip 24 and placing it in the position shown in FIG. 2B. Further movement of lever 18 toward handle 12 moves link 58, hammer extension 56 and hammer 26 further distally, thereby closing the distal-most clip 24 as in FIG. 2C. As lever 18 is then returned to its original position, link 58 is pulled in the proximal direction, pulling both hammer 26 and belt puller 38 in the proximal direction. Belt puller 38 engages retainers 32 on belt 30, as described above, thereby pulling the non-clip-carrying side of the belt 30 in the proximal direction, with the clip-carrying side of the belt 30 on which clips 14 are retained being advanced in the distal direction. In this manner the steps of advancing the clips in the barrel, positioning the distal-most clip in the anvil, and closing the distal-most clip are all performed by actuating a single lever on handle 12.

Referring to FIGS. 10A-10C, the ratcheting feature of the invention will now be described. Within handle 12, lever 18 has a ratcheting mechanism 20 including a grooved path 19 and a pawl 21 following grooved path 19. Pawl 21 is laterally flexible and resilient so as to follow the contours of path 19, while having compressive strength to prevent movement of lever 18 in the reverse direction. Grooved path 19 has a contour as shown in FIGS. 10B and 10C, including a series of sloping sections terminating in vertical cliffs. Pawl 21 has a hooked end portion 23 which follows the contour of grooved path 19, being guided up the successive ridges and over each cliff. When handle 18 is in its fully outward position such that clips 14 and hammer 26 are in the positions shown in FIGS. 2A and 5A, hook 23 of pawl 21 is at point 84 of FIGS. 10B and 10C. As lever 18 is moved toward handle 12, hook 23 follows the ridge from point 84 and over a cliff at point 86 as shown in FIG. 10B. Point 86 corresponds to the position of FIGS. 3A and 5B. As lever 18 is further moved toward handle 12, hook 23 is moved to position 88, corresponding to FIGS. 4A and 5C.

A spring 80 between arm 82 of lever 18 and anchor point 90 of handle 12 allows lever 18 to return to its original position simply by releasing pressure. Referring to FIG. 10C, as lever 18 returns, hook 23 of pawl 21 moves from point 88 over a cliff to point 90 and then over a second cliff back to point 84.

It should be evident that the ratcheting mechanism as described prevents the return of lever 18 to its outward position when a clip has been positioned in the anvil before closing, as in FIGS. 3A or 5B, or midway through the closing action. This prevents more than one clip from being fed to the anvil at any one time, which could jam the device. Further, it permits the user to move a clip into position in the anvil before closing, as in FIGS. 3A and 5B, and release pressure on the lever 18 while the clip in anvil 16 is positioned around the duct or tissue to be ligated, without returning hammer 26 to its proximal position or advancing belt 30.

An additional feature of the invention is an indicator for indicating to the user that the barrel of the clip applier contains no more clips. In a preferred embodiment, the indicator comprises a feature on belt 30 similar to retainers 32 which stands a greater height from the surface of belt 30 than do retainers 32. Referring to FIG. 6B, when the raised feature (not shown) carried by belt 30 encounters stop 92 in tube half 50b, the raised feature is unable to proceed further, thereby stopping the belt from movement. This prevents lever 18 from returning to its released, outward position, leaving the lever in a position between fully-released and fully-depressed. This will signal to the user that all of the clips in barrel 10 have been applied. An unknowing user, however, might at this point attempt to pull lever 18 toward handle 12 in an effort to make lever 18 return to its fully-released position. For this reason, the cliff at point 90 in the ratcheting mechanism 20 as described above is provided. When the belt 30 is prevented from movement by the raised feature, hook 23 on pawl 21 will have traveled from position 88 in grooved path 82 over the cliff at point 90, but lever 18 will be unable to move further, leaving pawl 21 at point 90. In the absence of a cliff at point 90, the user could pull lever 18 toward handle 12 moving pawl 21 back into position 88, potentially jamming the device and/or confusing the user. Therefore, the cliff at point 90 ensures that when the raised feature on belt 30 has stopped the return movement of lever 18, no additional movement of lever 18 in either direction is possible.

Referring now to FIGS. 11A-11E, the surgical clip of the present invention will be described. In a preferred embodiment, the surgical clip comprises a pair of arched legs 140, 142, connected by a bridge portion 144. Long leg 140 is longer than short leg 142 by a distance d, which, in one embodiment, is preferably about 0.025 inches where the distance h from the bridge to the end of long leg 140 is about 0.29 inches.

By configuring the clip 14 with a longer leg 140, both legs of the clip can be formed into a curve conforming with that of anvil 16 and clip track 28, such that both legs in the closed configuration are parallel and tips 146, 148 are substantially even, as shown in FIG. 11F.

In a further embodiment, short leg 142 is cut at its distal tip 148 at an angle $\theta$, preferably about 45°. As illustrated in FIGS. 5A-5C and 6A, this angular feature serves to allow leg 142 (identified as leg 15a in FIG. 6A) to pass over stop 52 at the distal end of barrel in a continuous and controlled manner when leg 142 (15a) of clip 24 is pushed distally by hammer 26.

In a further preferred embodiment, the clip interior surface 150 has a plurality of surface features 152 for improving the grip of clip 14 on tissue. Preferably, the surface features 152 comprise curved or angled grooves, as shown in FIG. 11B, extending from one edge of the clip to the other, with bridge portion 144 being left substantially free of surface features. In this embodiment, the features extend to a depth of about ½ the thickness of the clip. In other embodiments, the surface features 152 may comprise slots or holes of various shapes and densities, drilled at various depths into clip 14, including completely through the thickness of the clip. To further improve clip performance, a channel 154 may be provided extending the length of the clip in a middle portion of its width. Preferably, channel 154 has arcuate or angled sidewalls as shown in FIG. 11E.

Alternative clip embodiments are illustrated in FIGS. 12A-12B. In these embodiments, a shorter leg 142 has one or more inverse arcuate portions 156 which deform during clip closure in such a way as to improve clamping of clip 14 on tissue.

In the method of the present invention, a clip applier as that illustrated in FIGS. 1-10 is provided, the clip applier having means for closing a clip, e.g. hammer 26 and anvil 16, the anvil 16 defining a slot open in the lateral direction, and means for advancing a clip to the closing means, e.g. belt 30 in barrel 10, shown in FIGS. 6 and 8. The clip applier is then positioned using handle 12 and/or rotating barrel 10 such that the slot in anvil 16 surrounds the tissue to which a clip is to be applied. A clip 14 is then advanced with its legs 15 pointing in the distal direction, as shown in FIGS. 2-4. The distal-most clip 24 is then rotated along track 28 in anvil 16 such that the tissue lies between the legs of the clip. Alternatively, the preceding three steps may be resequenced such that a clip is first advanced, then rotated, then positioned around the tissue when the clip is already in anvil 16. Finally, the clip is closed on the tissue.

In a further embodiment, the steps of rotating, closing and advancing clips are performed using a trigger, e.g. lever 18 on handle 12. Lever 18 is ratcheted in stages as described above, with a first stage corresponding to moving the lever to a partially depressed position toward handle 12 wherein a clip is rotated and positioned in anvil 16, a second stage corresponding to moving lever 18 to a fully-depressed position wherein a clip is closed by hammer 26, and a third stage corresponding to releasing lever 18 wherein clips are advanced on belt 30.

In another exemplary embodiment of the method of the present invention, the clip applier is repositioned, a second clip is advanced and rotated, and the clip is closed on the new site without removing the slot from the tissue. As described above, the clip applier advances clips facing distally then rotates the clips in anvil 16 to face in a lateral direction, thereby avoiding interference between the clip legs and any tissue positioned in the slot of anvil 16. This is a particular advantage of the present invention, allowing a surgeon to apply two or more clips along a section of tissue or duct by simply moving the slot in anvil 16 along the tissue or duct, without removing it therefrom.

The method of the present invention further provides for exerting tension on the tissue by pulling on the clip applier after the tissue has been positioned in the slot.

This can be done for several purposes. First, the tissue can be pulled away from nearby tissue to avoid interfering with that tissue when the clip is closed. Known clip appliers suffer from the inability to exert tension on tissue, since the jaws are generally oriented distally, so that tissue cannot be pulled away from other tissue which might get in the way of the clip. Second, by applying such tension to the tissue, the tissue can be repositioned for better visibility. This is particularly advantageous during laparoscopic procedures, where the camera position is frequently somewhat limited, and the ability to pull the tissue in view of the camera to observe clip closure is highly desirable.

The clip applier of the present invention is especially well-adapted to such tensioning, since a clip can be rotated into the slot either before tissue has been pulled into tension, or after the user has pulled the tissue into a desired position and the tissue is being held in tension. Using either technique, the clip can rotate into the slot without interfering with the tissue.

While the above is a complete description of the preferred embodiments of the invention, various alternatives, modifications, and equivalents may be used. Therefore, the above description should not be taken as limiting the scope of the invention which is defined by the appended claims.

What is claimed is:

1. Apparatus for applying clips having a pair of connected legs, the apparatus comprising:
   a shaft having a distal end and a proximal end;
   means for advancing clips along the shaft toward the distal end with the legs oriented in a distal direction;
   means at the distal end of the shaft for rotating the clips relative to the shaft to orient the legs in a lateral direction; and
   means for closing the legs of the clips after said rotation.

2. Apparatus of claim 1 wherein the means for advancing comprises a movable belt disposed in the shaft, the belt having a plurality of retainers for holding clips.

3. The apparatus of claim 1 wherein the means for closing comprises an anvil mounted at the distal end of the shaft and a hammer movable against the anvil.

4. The apparatus of claim 3 further comprising means disposed at the proximal end of the shaft for actuating the hammer.

5. The apparatus of claim 4 wherein the means for actuating the hammer further actuates the means for rotating and the means for advancing.

6. The apparatus of claim 5 wherein the means for actuating comprises a lever pivotally mounted to a handle, the lever pivotable in at least two stages, said stages comprising a first stage for closing the clips and a second stage for advancing the clips.

7. Apparatus for applying surgical clips having a pair of connected legs, the apparatus comprising:
   a shaft having a distal end and a proximal end;
   an anvil disposed at the distal end of the shaft, the anvil having a forming surface oriented at an angle of at least 5° relative to the shaft;
   a handle disposed at the proximal end of the shaft;
   means for advancing clips along the shaft toward the anvil with the legs oriented in a distal direction;
   means on the shaft proximate the anvil for rotating the clip relative to the shaft to position a first leg of the clip adjacent said forming surface of the anvil;
   a hammer mounted on the shaft for engaging a second leg of the clip after said rotation; and
   an actuator coupled to the handle for translating the hammer relative to the anvil to close the legs of the clip.

8. The apparatus of claim 7 wherein the means for advancing clips comprises a movable belt, the belt having a plurality of retainers for holding the clips.

9. The apparatus of claim 8 wherein the belt is metal.

10. The apparatus of claim 8 further comprising means for disengaging a clip from the belt and for positioning the clip for initial engagement by the hammer.

11. The apparatus of claim 10 wherein the means for rotating comprises:
    a foot for engaging the second leg of a clip; and
    a curved track for engaging the first leg of the clip, wherein the hammer pushes the clip in the distal direction from the means for disengaging, the foot obstructs movement of the second leg, and the track guides the first leg to said forming surface, thereby rotating the clip about the foot.

12. The apparatus of claim 10 wherein the belt is disposed in a lateral portion of the shaft and the hammer is translated along a central axis of the shaft, the means for disengaging transferring a clip from the belt in the lateral portion to a position along the central axis.

13. The apparatus of claim 10 wherein the means for disengaging further comprises means for aligning the clip in a distal direction as it is pushed by the hammer.

14. The apparatus of claim 8 further comprising means for indicating when no clips remain in the appartus.

15. The apparatus of claim 14 wherein the means for indicting comprises means for preventing movement of the actuator when no clips remain.

16. The apparatus of claim 15 wherein the means for preventing movement comprises a raised feature on a surface of the belt and a stop on the shaft overlying the surface, the feature engaging the stop when no clips remain in the apparatus.

17. The apparatus of claim 7 wherein the actuator comprises means for advancing the hammer through three stages, the stages comprising:
    a first stage wherein a first clip is rotated;
    a second stage wherein the first clip is closed; and
    a third stage wherein a second clip is advanced to the means for rotating.

18. The apparatus of claim 7 further comprising means for rotating the shaft about a longitudinal axis.

19. The apparatus of claim 18 wherein the means for rotating the shaft comprises a knob fixed to the perimeter of the shaft proximate to the handle.

20. The apparatus of claim 7 wherein the shaft is detachably mounted to the handle.

21. The apparatus of claim 7 wherein the means for rotating rotates the clip about an axis perpendicular to and intersecting a planar region between and including the legs of the clip being rotated.

22. The apparatus of claim 7 wherein the forming surface of the anvil is curved, the distal end of the hammer having a corresponding curved shape so as to form both legs of the clip into a curve when the clip is closed.

23. The apparatus of claim 7 wherein the forming surface is generally perpendicular to said distal direction.

24. The apparatus of claim 7 wherein the forming surface is at an angle of 45° relative to said distal direction.

25. The apparatus of claim 7 wherein the shaft and the anvil are configured so as to pass through an opening having a diameter of 10 mm and wherein the legs of the clip are at least 0.29 inches in length.

26. A method of applying surgical clips to body tissue, the clips having a pair of connected legs, the method comprising:
providing a clip applier having means for closing a clip and means for advancing a clip to the closing means, the means for closing defining a slot open in a lateral direction;
positioning the clip applier such that the slot surrounds the tissue to which a clip will be applied;
advancing a clip with legs oriented in a distal direction;
rotating the clip into the slot such that the tissue lies between the legs of the clip; and
closing the clip on the tissue.

27. The method of claim 26 wherein the clip applier further comprises an actuator, wherein the step of rotating comprises moving the actuator from a first position to a second position, the step of closing comprises moving the actuator from the second position to a third position, and the step of advancing comprises returning the actuator to the first position.

28. The method of claim 26 further comprising:
repositioning the clip applier;
advancing and rotating a second clip without removing the slot from the tissue; and
closing the second clip on the tissue.

29. The method of claim 26 wherein said step of positioning further comprises rotating the clip about an axis parallel to said distal direction.

30. The method of claim 26 further comprising exerting tension on the tissue by pulling on the clip applier after the step of positioning.

31. The method of claim 30 wherein a clip is rotated into the slot while the tissue is in tension in the slot.

32. The method of claim 30 wherein said step of exerting tension further comprises positioning the tissue away from other tissue to avoid interference therewith.

33. The method of claim 30 further comprising visualizing the step of closing the clip using a camera, wherein the step of exerting tension repositions the tissue within view of the camera to facilitate visualization.

* * * * *